(12) United States Patent
Sun et al.

(10) Patent No.: US 8,338,636 B2
(45) Date of Patent: Dec. 25, 2012

(54) HYDROGENATION AND ESTERIFICATION TO FORM DIESTERS

(75) Inventors: Yanhui Sun, Wilmington, DE (US); Richard P. Beatty, Newark, DE (US)

(73) Assignee: Invista North America S.A R.L., Wilmington, DE (US)

( * ) Notice: Subject to any disclaimer, the term of this patent is extended or adjusted under 35 U.S.C. 154(b) by 349 days.

(21) Appl. No.: 12/851,296

(22) Filed: Aug. 5, 2010

(65) Prior Publication Data
US 2011/0207959 A1   Aug. 25, 2011

Related U.S. Application Data

(60) Provisional application No. 61/232,096, filed on Aug. 7, 2009.

(51) Int. Cl.
*C07C 67/08* (2006.01)
*C07C 69/347* (2006.01)

(52) U.S. Cl. .................................. 560/204; 560/191

(58) Field of Classification Search .......... None
See application file for complete search history.

(56) References Cited

U.S. PATENT DOCUMENTS

| | | |
|---|---|---|
| 2,768,132 A | 10/1956 | Halliwell |
| 3,370,082 A | 2/1968 | Eisfeld et al. |
| 3,496,215 A | 2/1970 | Drinkard et al. |
| 3,496,217 A | 2/1970 | Drinkard, Jr. et al. |
| 3,496,218 A | 2/1970 | Drinkard, Jr. |
| 3,522,288 A | 7/1970 | Drinkard, Jr. et al. |
| 3,536,748 A | 10/1970 | Drinkard, Jr. et al. |
| 3,551,474 A | 12/1970 | Drinkard et al. |
| 3,564,040 A | 2/1971 | Downing et al. |
| 3,579,560 A | 5/1971 | Drinkard et al. |
| 3,655,723 A | 4/1972 | Drinkard, Jr. et al. |
| 3,694,485 A | 9/1972 | Drinkard, Jr. et al. |
| 3,752,839 A | 8/1973 | Drinkard, Jr. et al. |
| 3,766,231 A | 10/1973 | Gosser et al. |
| 3,766,237 A | 10/1973 | Chia et al. |
| 3,766,241 A | 10/1973 | Drinkard, Jr. et al. |
| 3,773,809 A | 11/1973 | Walter |
| 3,775,461 A | 11/1973 | Drinkard, Jr. et al. |
| 3,798,256 A | 3/1974 | King et al. |
| 3,818,067 A | 6/1974 | Downing et al. |
| 3,818,068 A | 6/1974 | Wells |
| 3,830,830 A | 8/1974 | Cleveland et al. |
| 3,846,474 A | 11/1974 | Mok |
| 3,849,472 A | 11/1974 | Waddan |
| 3,850,973 A | 11/1974 | Seidel et al. |
| 3,853,754 A | 12/1974 | Gosser |
| 3,853,948 A | 12/1974 | Drinkard, Jr. et al. |
| 3,864,380 A | 2/1975 | King et al. |
| 3,869,501 A | 3/1975 | Waddan |
| 3,920,721 A | 11/1975 | Gosser |
| 3,927,056 A | 12/1975 | Gosser |
| 3,947,487 A | 3/1976 | Crooks |
| 4,045,495 A | 8/1977 | Nazarenko et al. |
| 4,046,815 A | 9/1977 | Nazarenko |
| 4,076,756 A | 2/1978 | Nazarenko et al. |

(Continued)

FOREIGN PATENT DOCUMENTS

AU    6522096    2/1997

(Continued)

*Primary Examiner* — Paul A Zucker

(57) ABSTRACT

A process is disclosed which employs hydrogenation and esterification to form alkyl diesters. The process subjects an unrefined or otherwise not purified composition comprising maleic anhydride production residue to the processes of hydrogenation and esterification and forming diesters at high conversion efficiency.

21 Claims, 1 Drawing Sheet

U.S. PATENT DOCUMENTS

| | | | |
|---|---|---|---|
| 4,087,452 A | 5/1978 | Kuntz | |
| 4,146,555 A | 3/1979 | Kershaw | |
| 4,147,717 A | 4/1979 | Kershaw | |
| 4,177,215 A | 12/1979 | Seidel | |
| 4,210,558 A | 7/1980 | Crooks | |
| 4,230,634 A | 10/1980 | Benzie et al. | |
| 4,240,976 A | 12/1980 | Benzie et al. | |
| 4,251,468 A | 2/1981 | Nazarenko | |
| 4,328,172 A | 5/1982 | Rapoport | |
| 4,330,483 A | 5/1982 | Rapoport | |
| 4,339,395 A | 7/1982 | Barnette et al. | |
| 4,371,474 A | 2/1983 | Rapoport | |
| 4,382,038 A | 5/1983 | McGill | |
| 4,385,007 A | 5/1983 | Shook, Jr. | |
| 4,416,824 A | 11/1983 | Reimer et al. | |
| 4,416,825 A | 11/1983 | Ostermaier | |
| 4,434,316 A | 2/1984 | Barnette | |
| 4,539,302 A | 9/1985 | Leyendecker et al. | |
| 4,705,881 A | 11/1987 | Rapoport | |
| 4,749,801 A | 6/1988 | Bealty et al. | |
| 4,774,353 A | 9/1988 | Hall et al. | |
| 4,874,884 A | 10/1989 | McKinney et al. | |
| 4,990,645 A | 2/1991 | Back et al. | |
| 5,107,012 A | 4/1992 | Grunewald | |
| 5,302,756 A | 4/1994 | McKinney | |
| 5,312,959 A | 5/1994 | Sieja et al. | |
| 5,449,807 A | 9/1995 | Druliner | |
| 5,488,129 A | 1/1996 | Huser et al. | |
| 5,512,695 A | 4/1996 | Kreutzer et al. | |
| 5,512,696 A | 4/1996 | Kreutzer et al. | |
| 5,523,453 A | 6/1996 | Breikss | |
| 5,543,536 A | 8/1996 | Tam | |
| 5,663,369 A | 9/1997 | Kreutzer et al. | |
| 5,688,986 A | 11/1997 | Tam et al. | |
| 5,696,280 A | 12/1997 | Shapiro | |
| 5,709,841 A | 1/1998 | Reimer | |
| 5,723,641 A | 3/1998 | Tam et al. | |
| 5,773,637 A | 6/1998 | Cicha et al. | |
| 5,821,378 A | 10/1998 | Foo et al. | |
| 5,847,191 A | 12/1998 | Bunel et al. | |
| 5,856,555 A | 1/1999 | Huser et al. | |
| 5,908,805 A | 6/1999 | Huser et al. | |
| 5,959,135 A | 9/1999 | Garner et al. | |
| 6,090,987 A | 7/2000 | Billig et al. | |
| 6,121,184 A | 9/2000 | Druliner et al. | |
| 6,147,247 A | 11/2000 | Voit et al. | |
| 6,169,198 B1 | 1/2001 | Fischer et al. | |
| 6,171,996 B1 | 1/2001 | Garner et al. | |
| 6,197,992 B1 | 3/2001 | Fischer et al. | |
| 6,242,633 B1 | 6/2001 | Fischer et al. | |
| 6,284,865 B1 | 9/2001 | Tam et al. | |
| 6,307,109 B1 | 10/2001 | Kanel et al. | |
| 6,355,833 B2 | 3/2002 | Fischer et al. | |
| 6,461,481 B1 | 10/2002 | Barnette et al. | |
| 6,469,194 B2 | 10/2002 | Burattin et al. | |
| 6,521,778 B1 | 2/2003 | Fischer et al. | |
| 6,646,148 B1 | 11/2003 | Kreutzer | |
| 6,660,877 B2 | 12/2003 | Lenges et al. | |
| 6,737,539 B2 | 5/2004 | Lenges et al. | |
| 6,753,440 B2 | 6/2004 | Druliner et al. | |
| 6,770,770 B1 | 8/2004 | Baumann et al. | |
| 6,846,945 B2 | 1/2005 | Lenges et al. | |
| 6,852,199 B2 | 2/2005 | Jungkamp et al. | |
| 6,855,799 B2 | 2/2005 | Tam et al. | |
| 6,897,329 B2 | 5/2005 | Jackson et al. | |
| 6,984,604 B2 | 1/2006 | Cobb et al. | |
| 7,022,866 B2 | 4/2006 | Bartsch et al. | |
| 7,067,685 B2 | 6/2006 | Bartsch et al. | |
| 7,084,293 B2 | 8/2006 | Rosier et al. | |
| 7,084,294 B2 | 8/2006 | Jungkamp et al. | |
| 7,098,358 B2 | 8/2006 | Burattin et al. | |
| 7,105,696 B2 | 9/2006 | Burattin et al. | |
| 7,253,298 B2 | 8/2007 | Galland et al. | |
| 7,345,006 B2 | 3/2008 | Bartsch et al. | |
| 7,381,845 B2 | 6/2008 | Weiskopf et al. | |
| 7,439,381 B2 | 10/2008 | Jungkamp et al. | |
| 7,442,825 B2 | 10/2008 | Galland et al. | |
| 7,470,805 B2 | 12/2008 | Rosier et al. | |
| 7,521,575 B2 | 4/2009 | Bartsch et al. | |
| 7,528,275 B2 | 5/2009 | Bartsch et al. | |
| 7,538,240 B2 | 5/2009 | Jungkamp et al. | |
| 7,541,486 B2 | 6/2009 | Scheidel et al. | |
| 7,700,795 B2 | 4/2010 | Haderlein et al. | |
| 2003/0135014 A1 | 7/2003 | Radu et al. | |
| 2003/0212298 A1 | 11/2003 | Brasse et al. | |
| 2004/0063991 A1 | 4/2004 | Burattin et al. | |
| 2004/0176622 A1 | 9/2004 | Bartsch et al. | |
| 2004/0235648 A1 | 11/2004 | Bartsch et al. | |
| 2004/0260112 A1 | 12/2004 | Basset et al. | |
| 2005/0090677 A1 | 4/2005 | Bartsch et al. | |
| 2005/0090678 A1 | 4/2005 | Bartsch et al. | |
| 2005/0247624 A1 | 11/2005 | Jungkamp et al. | |
| 2006/0142609 A1 | 6/2006 | Bourgeois et al. | |
| 2006/0175189 A1 | 8/2006 | Gerber et al. | |
| 2006/0252955 A1 | 11/2006 | Rosier et al. | |
| 2006/0258873 A1 | 11/2006 | Rosier et al. | |
| 2006/0258874 A1 | 11/2006 | Bartsch et al. | |
| 2006/0264651 A1 | 11/2006 | Bartsch et al. | |
| 2007/0060766 A1 | 3/2007 | Bartsch et al. | |
| 2007/0073071 A1 | 3/2007 | Haderlein et al. | |
| 2007/0083057 A1 | 4/2007 | Haderlein et al. | |
| 2007/0088173 A1 | 4/2007 | Haderlein et al. | |
| 2007/0112215 A1 | 5/2007 | Jungkamp et al. | |
| 2007/0155977 A1 | 7/2007 | Jungkamp et al. | |
| 2007/0155978 A1 | 7/2007 | Jungkamp et al. | |
| 2007/0155980 A1 | 7/2007 | Scheidel et al. | |
| 2008/0015378 A1 | 1/2008 | Foo et al. | |
| 2008/0015380 A1 | 1/2008 | Foo et al. | |
| 2008/0015381 A1 | 1/2008 | Foo et al. | |
| 2008/0015382 A1 | 1/2008 | Foo et al. | |
| 2008/0071105 A1 | 3/2008 | Bartsch et al. | |
| 2008/0076944 A1 | 3/2008 | Bartsch et al. | |
| 2008/0083607 A1 | 4/2008 | Deckert et al. | |
| 2008/0221351 A1 | 9/2008 | Bartsch et al. | |
| 2008/0227214 A1 | 9/2008 | Jungkamp et al. | |
| 2008/0227998 A1 | 9/2008 | Scheidel et al. | |
| 2008/0242883 A1 | 10/2008 | Jungkamp et al. | |
| 2008/0242885 A1 | 10/2008 | Jungkamp et al. | |
| 2008/0242886 A1 | 10/2008 | Bartsch et al. | |
| 2008/0275266 A1 | 11/2008 | Bartsch et al. | |
| 2008/0281119 A1 | 11/2008 | Scheidel et al. | |
| 2008/0281120 A1 | 11/2008 | Jungkamp et al. | |
| 2009/0054671 A1 | 2/2009 | Haderlein et al. | |

FOREIGN PATENT DOCUMENTS

| | | |
|---|---|---|
| AU | 199665220 A | 2/1997 |
| CA | 1324613 C | 11/1993 |
| CA | 2462720 A1 | 4/2003 |
| CA | 2552862 A1 | 8/2005 |
| CN | 1113854 A | 12/1995 |
| CN | 1145531 A | 3/1997 |
| CN | 1146166 A | 3/1997 |
| CN | 1146762 A | 4/1997 |
| CN | 1159106 A | 9/1997 |
| CN | 1159799 A | 9/1997 |
| CN | 1163606 A | 10/1997 |
| CN | 1169143 A | 12/1997 |
| CN | 1173935 A | 2/1998 |
| CN | 1179147 A | 4/1998 |
| CN | 1198151 A | 11/1998 |
| CN | 1204111 A | 1/1999 |
| CN | 1206357 A | 1/1999 |
| CN | 1211931 A | 3/1999 |
| CN | 1045591 C | 10/1999 |
| CN | 1236355 A | 11/1999 |
| CN | 1047163 C | 12/1999 |
| CN | 1245489 A | 2/2000 |
| CN | 1247102 A | 3/2000 |
| CN | 1052718 C | 5/2000 |
| CN | 1265094 A | 8/2000 |
| CN | 1266424 A | 9/2000 |
| CN | 1270543 A | 10/2000 |
| CN | 1068307 C | 7/2001 |
| CN | 1304334 A | 7/2001 |
| CN | 1069310 C | 8/2001 |
| CN | 1072980 C | 10/2001 |
| CN | 1076342 C | 12/2001 |

| | | | | | | | |
|---|---|---|---|---|---|---|---|
| CN | 1327881 | A | 12/2001 | CN | 100364666 | C | 1/2008 |
| CN | 1331843 | A | 1/2002 | CN | 101343211 | | 1/2009 |
| CN | 1333745 | A | 1/2002 | CN | 101343211 | A * | 1/2009 |
| CN | 1082946 | C | 4/2002 | DE | 1807088 | U | 3/1960 |
| CN | 1344180 | A | 4/2002 | DE | 1807088 | A1 | 6/1969 |
| CN | 1356335 | A | 7/2002 | DE | 2055747 | A1 | 5/1971 |
| CN | 1387534 | A | 12/2002 | DE | 1593277 | B2 | 8/1973 |
| CN | 1099912 | C | 1/2003 | DE | 1593277 | C3 | 3/1974 |
| CN | 1390241 | A | 1/2003 | DE | 2700904 | C2 | 10/1983 |
| CN | 1103613 | C | 3/2003 | DE | 68909466 | T2 | 3/1994 |
| CN | 1106218 | C | 4/2003 | DE | 10136488 | A1 | 2/2003 |
| CN | 1108643 | C | 5/2003 | DE | 10150285 | A1 | 4/2003 |
| CN | 1427807 | A | 7/2003 | DE | 10350999 | A1 | 6/2005 |
| CN | 1449400 | A | 10/2003 | DE | 102004004696 | A1 | 8/2005 |
| CN | 1461295 | A | 12/2003 | EP | 0001899 | B1 | 3/1982 |
| CN | 1471510 | A | 1/2004 | EP | 0190424 | | 8/1986 |
| CN | 1141285 | C | 3/2004 | EP | 123438 | B1 | 7/1987 |
| CN | 1142224 | C | 3/2004 | EP | 160296 | B1 | 10/1988 |
| CN | 1144781 | C | 4/2004 | EP | 268448 | B1 | 9/1991 |
| CN | 1487917 | A | 4/2004 | EP | 510689 | B1 | 10/1992 |
| CN | 1152855 | C | 6/2004 | EP | 248643 | B1 | 3/1993 |
| CN | 1535179 | A | 10/2004 | EP | 336314 | B1 | 9/1993 |
| CN | 1564807 | A | 1/2005 | EP | 464691 | B1 | 12/1993 |
| CN | 1568225 | A | 1/2005 | EP | 0728731 | | 8/1996 |
| CN | 1568226 | A | 1/2005 | EP | 675871 | B1 | 4/1997 |
| CN | 1617892 | A | 5/2005 | EP | 634395 | B1 | 9/1997 |
| CN | 1617900 | A | 5/2005 | EP | 650959 | B1 | 9/1997 |
| CN | 1212293 | C | 7/2005 | EP | 784610 | B1 | 2/1999 |
| CN | 1639176 | A | 7/2005 | EP | 757672 | B1 | 6/1999 |
| CN | 1213051 | C | 8/2005 | EP | 792259 | B1 | 8/1999 |
| CN | 1665776 | A | 9/2005 | EP | 804412 | B1 | 12/1999 |
| CN | 1670139 | A | 9/2005 | EP | 1000019 | A1 | 5/2000 |
| CN | 1674989 | A | 9/2005 | EP | 1001928 | A1 | 5/2000 |
| CN | 1675172 | A | 9/2005 | EP | 1003716 | A1 | 5/2000 |
| CN | 1222358 | C | 10/2005 | EP | 1019190 | A1 | 7/2000 |
| CN | 1732148 | A | 2/2006 | EP | 755302 | B1 | 10/2000 |
| CN | 1735460 | A | 2/2006 | EP | 929513 | B1 | 4/2001 |
| CN | 1245489 | C | 3/2006 | EP | 881924 | B1 | 5/2001 |
| CN | 1740183 | A | 3/2006 | EP | 854858 | B1 | 6/2001 |
| CN | 1745062 | A | 3/2006 | EP | 815073 | B1 | 7/2001 |
| CN | 1767895 | A | 5/2006 | EP | 1144114 | A3 | 9/2001 |
| CN | 1260009 | C | 6/2006 | EP | 1091804 | B1 | 2/2002 |
| CN | 1266424 | C | 7/2006 | EP | 944585 | B1 | 4/2002 |
| CN | 1270543 | C | 8/2006 | EP | 1000019 | B1 | 2/2003 |
| CN | 1274671 | C | 9/2006 | EP | 911339 | B1 | 4/2003 |
| CN | 1274699 | C | 9/2006 | EP | 1216268 | B1 | 11/2003 |
| CN | 1835915 | A | 9/2006 | EP | 1350788 | A3 | 11/2003 |
| CN | 1279088 | C | 10/2006 | EP | 1003607 | B1 | 12/2003 |
| CN | 1847288 | A | 10/2006 | EP | 1003716 | B1 | 2/2004 |
| CN | 1283620 | C | 11/2006 | EP | 1313743 | B1 | 3/2004 |
| CN | 1857775 | A | 11/2006 | EP | 1414567 | A1 | 5/2004 |
| CN | 1289539 | C | 12/2006 | EP | 1427695 | A1 | 6/2004 |
| CN | 1293942 | C | 1/2007 | EP | 1438133 | A1 | 7/2004 |
| CN | 1906150 | A | 1/2007 | EP | 1019190 | B1 | 12/2004 |
| CN | 1914154 | A | 2/2007 | EP | 1140801 | B1 | 2/2005 |
| CN | 1914155 | A | 2/2007 | EP | 1395547 | B1 | 3/2005 |
| CN | 1914156 | A | 2/2007 | EP | 1001928 | B1 | 4/2005 |
| CN | 1914157 | A | 2/2007 | EP | 1521736 | A1 | 4/2005 |
| CN | 1914158 | A | 2/2007 | EP | 1521737 | A1 | 4/2005 |
| CN | 1914159 | A | 2/2007 | EP | 1521738 | A2 | 4/2005 |
| CN | 1914160 | A | 2/2007 | EP | 1603865 | A1 | 12/2005 |
| CN | 1914161 | A | 2/2007 | EP | 1324976 | B1 | 2/2006 |
| CN | 1914162 | A | 2/2007 | EP | 1214975 | B1 | 3/2006 |
| CN | 1914165 | A | 2/2007 | EP | 1324978 | B1 | 3/2006 |
| CN | 1914166 | A | 2/2007 | EP | 1648860 | A1 | 4/2006 |
| CN | 1914167 | A | 2/2007 | EP | 891323 | B1 | 6/2006 |
| CN | 1914216 | A | 2/2007 | EP | 1226147 | B1 | 6/2006 |
| CN | 1307237 | C | 3/2007 | EP | 1438317 | B1 | 6/2006 |
| CN | 1315790 | C | 5/2007 | EP | 1682561 | A1 | 7/2006 |
| CN | 1318432 | C | 5/2007 | EP | 1448668 | B1 | 8/2006 |
| CN | 1997624 | A | 7/2007 | EP | 1587621 | B1 | 8/2006 |
| CN | 1331843 | C | 8/2007 | EP | 1713759 | A1 | 10/2006 |
| CN | 101020641 | A | 8/2007 | EP | 1713761 | A1 | 10/2006 |
| CN | 101035799 | A | 9/2007 | EP | 1713762 | A1 | 10/2006 |
| CN | 101043946 | A | 9/2007 | EP | 1713766 | A1 | 10/2006 |
| CN | 100348322 | C | 11/2007 | EP | 1716102 | A2 | 11/2006 |
| CN | 100351227 | C | 11/2007 | EP | 1716103 | A1 | 11/2006 |
| CN | 100352824 | C | 12/2007 | EP | 1716104 | A1 | 11/2006 |
| CN | 100361966 | C | 1/2008 | EP | 1716105 | A1 | 11/2006 |

| | | | | | | |
|---|---|---|---|---|---|---|
| EP | 1716106 | A1 | 11/2006 | JP | 1642102 C | 2/1992 |
| EP | 1716107 | A1 | 11/2006 | JP | 4012248 Y2 | 3/1992 |
| EP | 1716109 | A2 | 11/2006 | JP | 4057050 U | 5/1992 |
| EP | 1610893 | B1 | 3/2007 | JP | 4166155 A | 6/1992 |
| EP | 1621531 | B1 | 3/2007 | JP | 4230254 A | 8/1992 |
| EP | 1438132 | B1 | 4/2007 | JP | 4057050 B | 9/1992 |
| EP | 1799697 | A1 | 6/2007 | JP | 4060532 B | 9/1992 |
| EP | 1713764 | B1 | 8/2007 | JP | 4118676 U | 10/1992 |
| EP | 1713816 | B1 | 8/2007 | JP | 4128141 U | 11/1992 |
| EP | 1825914 | A1 | 8/2007 | JP | 1729140 C | 1/1993 |
| EP | 1448620 | B1 | 6/2008 | JP | 1811422 C | 12/1993 |
| EP | 1817108 | B1 | 6/2008 | JP | 7025841 Y2 | 6/1995 |
| EP | 1713760 | B1 | 7/2008 | JP | 7188144 A | 7/1995 |
| EP | 1571172 | B1 | 10/2008 | JP | 2037346 C | 3/1996 |
| EP | 1988998 | A1 | 11/2008 | JP | 8504814 A | 5/1996 |
| EP | 1265832 | B1 | 5/2009 | JP | 8157795 A | 6/1996 |
| EP | 1592659 | B1 | 7/2009 | JP | 2098106 C | 10/1996 |
| EP | 1586598 | B1 | 9/2009 | JP | 02521777 Y2 | 1/1997 |
| EP | 2098106 | A1 | 9/2009 | JP | 02623448 B2 | 6/1997 |
| EP | 1567478 | B1 | 10/2009 | JP | 9505586 A | 6/1997 |
| EP | 1682559 | B1 | 12/2009 | JP | 9512013 A | 12/1997 |
| EP | 1630166 | B1 | 2/2010 | JP | 10505101 A | 5/1998 |
| FR | 1544656 | A | 11/1968 | JP | 10506911 A | 7/1998 |
| FR | 2015115 | A5 | 4/1970 | JP | 10509954 A | 9/1998 |
| FR | 1603513 | A | 5/1971 | JP | 02818503 B2 | 10/1998 |
| FR | 2069411 | A5 | 9/1971 | JP | 10512879 A | 12/1998 |
| FR | 2845379 | B1 | 12/2004 | JP | 11501660 A | 2/1999 |
| FR | 2873696 | A1 | 2/2006 | JP | 11504262 A | 4/1999 |
| FR | 2873696 | B1 | 10/2006 | JP | 02911608 B2 | 6/1999 |
| GB | 0219474 | A | 7/1924 | JP | 11507297 A | 6/1999 |
| GB | 1104140 | A | 2/1968 | JP | 03001298 B2 | 1/2000 |
| GB | 1203702 | A | 9/1970 | JP | 03069915 B2 | 7/2000 |
| GB | 1213175 | A | 11/1970 | JP | 2001500135 A | 1/2001 |
| GB | 1429169 | A | 3/1976 | JP | 2001506250 A | 5/2001 |
| GB | 1429621 | A | 3/1976 | JP | 2001512097 A | 8/2001 |
| GB | 1436932 | A | 5/1976 | JP | 03205587 B2 | 9/2001 |
| GB | 1458322 | A | 12/1976 | JP | 2001516640 A | 10/2001 |
| GB | 1482909 | A | 8/1977 | JP | 03285878 B2 | 5/2002 |
| GB | 2007521 | A | 5/1979 | JP | 2002517473 A | 6/2002 |
| GB | 1565443 | A | 4/1980 | JP | 03320424 B2 | 9/2002 |
| GB | 1594694 | A | 8/1981 | JP | 2002533321 A | 10/2002 |
| GB | 2007521 | B | 6/1982 | JP | 03380543 B2 | 2/2003 |
| HK | 1025950 | A1 | 7/2003 | JP | 2003510385 A | 3/2003 |
| HK | 1026383 | A1 | 7/2004 | JP | 2003526688 A | 9/2003 |
| HK | 1052364 | A1 | 5/2007 | JP | 03478399 B2 | 12/2003 |
| JP | 48028423 | Y1 | 8/1973 | JP | 2004501058 A | 1/2004 |
| JP | 48028423 | B | 9/1973 | JP | 2004507550 A | 3/2004 |
| JP | 49043924 | Y1 | 12/1974 | JP | 03519410 B2 | 4/2004 |
| JP | 50059324 | U | 6/1975 | JP | 03535172 B2 | 6/2004 |
| JP | 50059326 | U | 6/1975 | JP | 03553952 B2 | 8/2004 |
| JP | 51007649 | B | 3/1976 | JP | 2004534032 A | 11/2004 |
| JP | 52012698 | B | 4/1977 | JP | 2004535929 A | 12/2004 |
| JP | 1013127 | C | 9/1980 | JP | 03621133 B2 | 2/2005 |
| JP | 55047031 | B | 11/1980 | JP | 2005503410 A | 2/2005 |
| JP | 57156454 | U | 10/1982 | JP | 2005505610 A | 2/2005 |
| JP | 57156455 | U | 10/1982 | JP | 2005505611 A | 2/2005 |
| JP | 57179144 | U | 11/1982 | JP | 2005510588 A | 4/2005 |
| JP | 1136333 | C | 2/1983 | JP | 2005510605 A | 4/2005 |
| JP | 58067658 | U | 5/1983 | JP | 2004509942X | 10/2005 |
| JP | 58126892 | U | 8/1983 | JP | 2005533095 A | 11/2005 |
| JP | 1170710 | C | 10/1983 | JP | 2005533096 A | 11/2005 |
| JP | 58159452 | U | 10/1983 | JP | 2005538075 A | 12/2005 |
| JP | 60044295 | A | 3/1985 | JP | 03739404 B2 | 1/2006 |
| JP | 60044295 | B | 10/1985 | JP | 2004534032X | 1/2006 |
| JP | 62294691 | A | 12/1987 | JP | 2004535929X | 1/2006 |
| JP | 63135363 | U | 9/1988 | JP | 2006000451 A | 1/2006 |
| JP | 1013127 | Y2 | 4/1989 | JP | 2006511591 A | 4/2006 |
| JP | 1209830 | A | 8/1989 | JP | 2006519797 A | 8/2006 |
| JP | 1136333 | U | 9/1989 | JP | 2006528616 A | 12/2006 |
| JP | 1050220 | B | 10/1989 | JP | 2007083057 A | 4/2007 |
| JP | 1173751 | U | 12/1989 | JP | 2007509885 A | 4/2007 |
| JP | 1565159 | C | 6/1990 | JP | 2007509886 A | 4/2007 |
| JP | 3001298 | B | 1/1991 | JP | 2007509887 A | 4/2007 |
| JP | 1615749 | C | 8/1991 | JP | 2007519516 A | 7/2007 |
| JP | 3205587 | A | 9/1991 | JP | 2007519663 A | 7/2007 |
| JP | 1627124 | C | 11/1991 | JP | 2007519664 A | 7/2007 |
| JP | 1627146 | C | 11/1991 | JP | 2007519666 A | 7/2007 |
| JP | 3069915 | B | 11/1991 | JP | 2007519667 A | 7/2007 |
| JP | 3285878 | A | 12/1991 | JP | 2007519670 A | 7/2007 |

| | | | | | | |
|---|---|---|---|---|---|---|
| JP | 2007519671 | A | 7/2007 | WO | WO9964155 A1 | 12/1999 |
| JP | 2007519672 | A | 7/2007 | WO | WO0001485 A2 | 1/2000 |
| JP | 2007519673 | A | 7/2007 | WO | WO0037431 A1 | 6/2000 |
| JP | 2007519674 | A | 7/2007 | WO | WO0121684 A1 | 3/2001 |
| JP | 2007519675 | A | 7/2007 | WO | WO0136429 A1 | 5/2001 |
| JP | 2007519677 | A | 7/2007 | WO | WO0168247 A2 | 9/2001 |
| JP | 2007522122 | A | 8/2007 | WO | WO0211108 A1 | 2/2002 |
| JP | 04012248 | B2 | 11/2007 | WO | WO0213964 A2 | 2/2002 |
| JP | 2006515323X | | 2/2008 | WO | WO0218392 A1 | 3/2002 |
| JP | 04057050 | B2 | 3/2008 | WO | WO0226698 A1 | 4/2002 |
| JP | 04060532 | B2 | 3/2008 | WO | WO0230854 A2 | 4/2002 |
| JP | 2006512918X | | 3/2008 | WO | WO02053527 A1 | 7/2002 |
| JP | 2008515831 | A | 5/2008 | WO | WO02092551 A2 | 11/2002 |
| JP | 2008516907 | A | 5/2008 | WO | WO03011457 A1 | 2/2003 |
| JP | 04118676 | B2 | 7/2008 | WO | WO03018540 A1 | 3/2003 |
| JP | 04128141 | B2 | 7/2008 | WO | WO03024919 A1 | 3/2003 |
| JP | 04166155 | B2 | 10/2008 | WO | WO03031392 A1 | 4/2003 |
| JP | 04230254 | B2 | 2/2009 | WO | WO03033141 A1 | 4/2003 |
| KR | 198802621 | Y1 | 7/1988 | WO | WO03033509 A1 | 4/2003 |
| KR | 198802296 | B | 10/1988 | WO | WO03046019 A1 | 6/2003 |
| KR | 198802296 | B1 | 10/1988 | WO | WO03046049 A1 | 6/2003 |
| KR | 199003458 | B1 | 5/1990 | WO | WO03068729 A1 | 8/2003 |
| KR | 199008166 | B1 | 11/1990 | WO | WO03076394 A1 | 9/2003 |
| KR | 199104132 | B1 | 6/1991 | WO | WO2004007431 A1 | 1/2004 |
| KR | 199205087 | Y1 | 7/1992 | WO | WO2004007432 A1 | 1/2004 |
| KR | 2006132885 | A | 12/2006 | WO | WO2004007435 A2 | 1/2004 |
| MX | 2004PA002764 | A | 6/2004 | WO | WO2004007508 A2 | 1/2004 |
| NL | 197700262 | A | 7/1977 | WO | WO01068247 A8 | 6/2004 |
| NL | 188158 | C | 4/1992 | WO | WO2004060855 A1 | 7/2004 |
| SU | 677650 | A | 7/1979 | WO | WO2004064994 A2 | 8/2004 |
| TW | 387874 | B | 4/2000 | WO | WO2004065352 A2 | 8/2004 |
| TW | 400249 | B | 8/2000 | WO | WO2004080924 A2 | 9/2004 |
| TW | 453983 | B | 9/2001 | WO | WO2004080948 A1 | 9/2004 |
| TW | 453985 | B | 9/2001 | WO | WO2004087314 A1 | 10/2004 |
| TW | 455576 | B | 9/2001 | WO | WO2005019160 A1 | 3/2005 |
| TW | 457244 | B | 10/2001 | WO | WO2005042156 A1 | 5/2005 |
| TW | 458959 | B | 10/2001 | WO | WO2005042157 A2 | 5/2005 |
| TW | 519496 | B | 2/2003 | WO | WO2005042547 A1 | 5/2005 |
| TW | 527340 | B | 4/2003 | WO | WO2005042549 A1 | 5/2005 |
| TW | 576837 | B | 2/2004 | WO | WO2005073167 A1 | 8/2005 |
| TW | 580489 | B | 3/2004 | WO | WO2005073168 A1 | 8/2005 |
| TW | 580490 | B | 3/2004 | WO | WO2005073169 A1 | 8/2005 |
| TW | 584623 | B | 4/2004 | WO | WO2005073170 A1 | 8/2005 |
| TW | 592821 | B | 6/2004 | WO | WO2005073171 A1 | 8/2005 |
| TW | 226345 | B | 1/2005 | WO | WO2005073172 A1 | 8/2005 |
| TW | 233438 | B | 6/2005 | WO | WO2005073173 A1 | 8/2005 |
| TW | 245780 | B | 12/2005 | WO | WO2005073174 A1 | 8/2005 |
| TW | 266650 | B | 11/2006 | WO | WO2005073175 A1 | 8/2005 |
| WO | WO7900193 | A1 | 4/1979 | WO | WO2005073176 A1 | 8/2005 |
| WO | WO9414752 | A1 | 7/1994 | WO | WO2005073178 A2 | 8/2005 |
| WO | WO9514659 | A1 | 6/1995 | WO | WO2005073179 A1 | 8/2005 |
| WO | WO9528228 | A1 | 10/1995 | WO | WO2005073241 A1 | 8/2005 |
| WO | WO9529153 | A1 | 11/1995 | WO | WO2006040023 A1 | 4/2006 |
| WO | WO9611182 | A1 | 4/1996 | WO | WO2006042675 A2 | 4/2006 |
| WO | WO9616022 | A1 | 5/1996 | WO | WO2005073166 A3 | 3/2007 |
| WO | WO9622968 | A1 | 8/1996 | WO | WO2007051374 A1 | 5/2007 |
| WO | WO9629303 | A1 | 9/1996 | WO | WO2007096274 A1 | 8/2007 |
| WO | WO9703040 | A1 | 1/1997 | WO | WO2007115936 | 10/2007 |
| WO | WO9712857 | A1 | 4/1997 | WO | WO2007115936 A2 | 10/2007 |
| WO | WO9724183 | A1 | 7/1997 | WO | WO2008008926 A2 | 1/2008 |
| WO | WO9736855 | A2 | 10/1997 | WO | WO2008008928 A2 | 1/2008 |
| WO | WO9811051 | A1 | 3/1998 | WO | WO2008008929 A2 | 1/2008 |
| WO | WO9827054 | A1 | 6/1998 | WO | WO2008008930 A2 | 1/2008 |
| WO | WO9906146 | A2 | 2/1999 | WO | WO2008028843 A1 | 3/2008 |
| WO | WO9906356 | | 2/1999 | WO | WO2008062058 A1 | 5/2008 |
| WO | WO9906359 | A1 | 2/1999 | | | |
| WO | WO9913983 | A1 | 3/1999 | | | |

\* cited by examiner

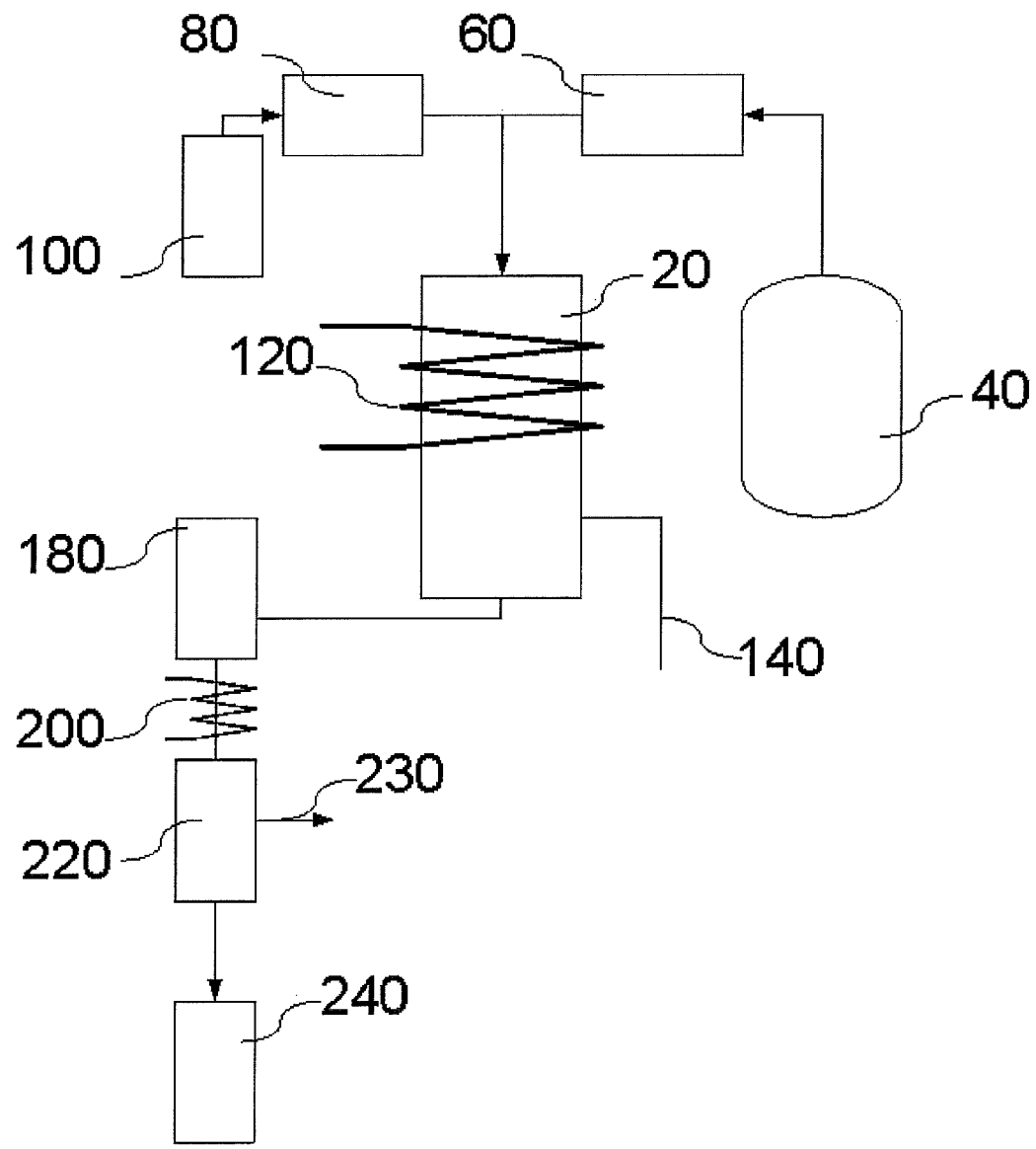

HYDROGENATION AND ESTERIFICATION TO FORM DIESTERS

CROSS-REFERENCE TO RELATED APPLICATIONS

This application claims benefit of priority from U.S. Provisional Application No. 61/232,096, filed on Aug. 7, 2009. This application hereby incorporates by reference U.S. Provisional Application No. 61/232,096 in its entirety.

FIELD OF THE INVENTION

The disclosures herein relate to process of chemical transformation employing hydrogenation and esterification to form diesters. More particularly these disclosures relate to subjecting a composition comprising a co-product stream from maleic anhydride manufacture to processes of hydrogenation and esterification and forming diesters at high conversion without prior purification of the composition.

BACKGROUND OF THE INVENTION

The class of dialkyl succinates is known and widely used in low volatility organic solvents and as versatile starting materials in synthesis. A member of this class is dimethyl succinate (herein after DMS). Known methods to provide DMS include direct esterification of succinic acid. However, the high cost of succinic acid makes this method not commercially attractive.

A more cost effective source of succinic acid is derived from dibasic acid (DBA), a co-product of adipic acid manufacture. Succinic acid, however, comprises only ca. 20 wt % of DBA, the remainder being glutaric and adipic acids. As a result, the preparation of DMS from this mixed acid DBA composition, while known, provides more glutarate and adipate diesters than DMS. Often demand for glutarate and adipate diesters is less than that for the more desirable DMS. In view of increasing demand for DMS and lessening demand for production of DBA, linked to production of adipic acid, it is very desirable to find low-cost routes to DMS.

Chinese patent document CN101343211 discloses a process for making butanediol or succinic acid diester from byproducts in maleic anhydride production. Steps include esterification of these byproducts, comprising substantially solid residue, maleic anhydride residue and/or crystallized wastewater, with $C_1$-$C_8$ monohydric alcohols in the presence of a catalyst; followed by distillation to recover a mixture of succinate diester, maleate diester and fumarate diester as a distillate; followed by reduction with hydrogen in the presence of a copper-based catalyst at 140-210° C. and 40-80 atmospheres; and finally distilling to obtain butanediol or succinic acid diester. A disadvantage of this process is that the distillation prior to reduction with hydrogen, which is a form of purification, requires a significant capital investment cost and high energy cost because the mixture of diesters must be vaporized and condensed in order to be recovered from higher boiling compounds as an overhead purified distillate. Thus it would be desirable to avoid the need for a distillation step prior to the step of reducing with hydrogen.

Accordingly, esterification of maleic anhydride often yields a high level of dialkyl fumarate, such as dimethyl fumarate, which has a melting point of 103° C. Therefore, it is technically more difficult to handle in a production facility than pure maleate diesters.

U.S. Pat. No. 3,830,830 (Cleveland et al.; assigned to Eastman) discloses production of dialkyl esters of succinic acid from substantially pure maleic anhydride by first hydrogenating maleic monomethyl ester. Steps further include high pressure esterification at 15-5000 pounds per square inch (psig) without a catalyst. The undesirable formation of dimethyl fumarate (by isomerization of maleate) is eliminated and the reported esterification yields of 86% and 91%, which may not be high enough for an economically and commercially viable process. In addition, esterification under high pressure often requires special equipment and is costly.

There remains in the art an unmet need for a simplified method to make dialkyl succinates which is readily commercialized in an economically desirable form. The disclosures herein provide a process for converting a mixture of maleic anhydride, succinic anhydride, maleic acid, succinic acid, fumaric acid, and other components, such as co-products or residues from maleic anhydride manufacture, which is commonly not utilized but incinerated or otherwise disposed, to a series of useful succinate diesters. A major distinction from known processes includes the hydrogenation of a complex mixture from maleic anhydride production residue, containing fumarate precursors such as fumaric acid, without any prior purification. This complex mixture from maleic anhydride production residue can also be esterified to form dialkyl maleate esters and dialkyl fumarate esters and then subjected to hydrogenation to form dialkyl succinates without any prior purification.

SUMMARY OF THE INVENTION

Disclosed is a process for preparing dialkyl succinate from co-products or residues obtained from maleic anhydride manufacture. In some embodiments, the co-products or residues comprise a mixture of maleic anhydride production residue. In some embodiments, the co-products or residues comprise maleic anhydride, succinic anhydride, and their corresponding acids. In some embodiments, the maleic anhydride production residue mixture comprises substantially about: 30 to 90 wt % maleic anhydride; 5 to 68 wt % fumaric acid; 0.4 to 2 wt % maleic acid; 0.1 to 0.5 wt % succinic anhydride; 0.05 to 0.5 wt % succinic acid; 0.1 to 1 wt % phthalic anhydride; 0.1 to 0.5 wt % fumaric monoaldehyde; 0.1 to 0.5 wt % 5-hydroxy-2-furanone; 0.5 to 1.5 wt % malic acid; 0.1 to 0.3 wt % o-xylene; 0.02 to 0.1 wt % acetic acid; a trace amount of methanol, ca. 250 ppm chloride, less than 100 ppm bromide, and other organic compounds not identified.

In some embodiments, the disclosures herein provide a process for making dialkyl succinate, comprising:
a. providing the mixture comprising about 30 to 90 wt % maleic anhydride and about 5 to 68 wt % fumaric acid;
b. contacting the mixture of (a) with an alkyl alcohol solvent in sufficient amount to form a solution and holding the solution at a temperature of from about 20° C. to about 250° C. for a holding time;
c. hydrogenating the solution of (b), in the absence of an intermediate distillation between (b) and (c), at hydrogenation conditions of temperature from about 50 to 200° C. under hydrogen pressure from about 50 to 1000 psig (about 450 to 7000 kPa) in the presence of a hydrogenation catalyst to form a hydrogenation product;
d. treating the hydrogenation product with alcohol at an esterification temperature of about 100° C. to 140° C. to form crude product containing dialkyl esters, wherein at least 85 percent of maleic anhydride, fumaric acid and their derivatives of (a) have been converted to dialkyl esters in the crude product; and
e. isolating dialkyl succinate from the crude product of (d).

In some embodiments, the mixture of (a) further comprises about 0.4 to 2 wt % maleic acid. In some embodiments, the mixture of (a) further comprises about 0.1 to 0.5 wt % succinic anhydride. In some embodiments, the mixture of (a) further comprises about 0.05 to 0.5 wt % succinic acid. In some embodiments, the mixture of (a) further comprises about 0.1 to 1 wt % phthalic anhydride. In some embodiments, the mixture of (a) further comprises about 0.1 to 0.5 wt % fumaric monoaldehyde. In some embodiments, the mixture of (a) further comprises about 0.1 to 0.5 wt % 5-hydroxy-2-furanone. In some embodiments, the mixture of (a) further comprises about 0.5 to 1.5 wt % malic acid. In some embodiments, the mixture of (a) further comprises about 0.1 to 0.3% o-xylene. In some embodiments, the mixture of (a) further comprises about 0.02 to 0.1 wt % acetic acid.

In some embodiments, the mixture comprising about 30 to 90 wt % maleic anhydride and about 5 to 68 wt % fumaric acid is maleic anhydride production residue.

In some process embodiments, the hydrogenation catalyst comprises palladium.

In some process embodiments, the contacting (b) or the esterification (d) is carried out in the presence of an esterification catalyst. In some embodiments, the esterification catalyst is an acid catalyst.

In some process embodiments, isolating dialkyl succinate from the crude product containing dialkyl esters is conducted by distillation. In some embodiments, the distillation comprises:
  a. distilling in a first distillation column the crude product containing dialkyl esters to separate a low-boiling overhead stream enriched in dialkyl esters from high-boiling acids and esters.
  b. distilling in a second distillation column the low-boiling overhead stream enriched dialkyl esters from the first distillation column to produce a low-boiling overhead stream enriched in dialkyl fumarate, a side-stream enriched in dialkyl succinate, and a bottoms stream containing higher boiling materials; and
  c. withdrawing the side-stream enriched in dialkyl succinate as the product.

In some embodiments, at least a portion of the low-boiling overhead stream enriched in dialkyl fumarate from the second distillation is recycled to the hydrogenating step.

In some embodiments, the distillation comprises:
  a. distilling in a distillation column the crude product containing dialkyl esters to produce a low-boiling overhead stream enriched in dialkyl fumarate;
  b. cooling the low-boiling overhead stream enriched in dialkyl fumarate to form condensed liquid and solids;
  c. separating the solids from the condensed liquid to form a condensed liquid substantially free of solids;
  d. returning at least a portion of the condensed liquid substantially free of solids to the distillation column.

In some embodiments, separating the solids from the condensed liquid to form a condensed liquid substantially free of solids is conducted by filtration. In some embodiments, separating the solids from the condensed liquid to form a condensed liquid substantially free of solids is conducted by crystallization.

In some embodiments, at least 95 weight percent of maleic anhydride, fumaric acid and their derivatives of the mixture (a) comprising about 30 to 90 wt % maleic anhydride and about 5 to 68 wt % fumaric acid have been converted to dialkyl esters in the crude product.

In some embodiments, the disclosures herein provide a dialkyl succinate composition prepared by the process embodiments described above.

BRIEF DESCRIPTION OF THE DRAWING

FIG. 1 is a simplified schematic representation of a fixed catalyst bed reactor for carrying out an embodiment of the continuous hydrogenation reaction disclosed herein.

DETAILED DESCRIPTION

Although the following detailed description contains many specifics for the purpose of illustration, a person of ordinary skill in the art will appreciate that many variations and alterations to the following details are within the scope of the herein disclosed embodiments.

Accordingly, the following embodiments are set forth without any loss of generality to, and without imposing limitations upon any claimed invention. Before the present disclosure is described in greater detail, it is to be understood that this disclosure is not limited to particular embodiments described, as such may vary. It is also to be understood that the terminology used herein is for the purpose of describing particular embodiments only, and is not intended to be limiting, since the scope of the present disclosure will be limited only by the appended claims.

The disclosures herein relate to an economically effective process for preparation of succinate dialkyl esters from a complex mixture of one or more co-products or residues from a commercial maleic anhydride production process, sometimes referred to herein as maleic anhydride production residue. An example of the one or more co-products or residues is maleic anhydride production bottom stream residue (e.g., heavy ends bottoms stream from the final maleic anhydride distillation column in a commercial maleic anhydride purification process). These disclosures provide a process comprising hydrogenation and esterification of a complex residue stream at greater than about 99.5% conversions without prior purification of the maleic anhydride production residue.

A distinction provided by the disclosures herein is the hydrogenation of a complex mixture from maleic anhydride production residue without prior purification. A main component in the maleic anhydride production residue stream is maleic anhydride, however, at least 10 to 18 other compounds including, for example, fumaric acid, may coexist in the mixture with it. In some embodiments, the maleic anhydride production residue stream contains about 30 to 89 weight % maleic anhydride. Without purification, the hydrogenation reaction of this mixture in methanol can be surprisingly fast at high conversion, ca. 99.7%. Esterification after hydrogenation may achieve about 99.5% completion. Alternatively, the maleic anhydride production residue can be esterified to obtain dialkyl esters at a high conversion, such as 99.5%, and then hydrogenated in the presence of a hydrogenation catalyst to form dialkyl succinates with up to 99.8% completion or more.

The step of contacting the maleic anhydride production residue mixture with an alkyl alcohol solvent can employ any amount of alkyl alcohol sufficient to form a solution. In some process embodiments, the amount of alkyl alcohol solvent is the amount required to make a solution having a concentration of from about 5 wt % to about 50 wt % maleic anhydride production residue mixture, for example from about 5 wt % to about 30 wt % maleic anhydride production residue mixture. Sufficient amount of alkyl alcohol solvent is added to ensure that the maleic anhydride production residue mixture remains in solution, which is particularly desired when there is a high concentration of fumaric acid in the maleic anhydride production residue mixture.

Holding the alkyl alcohol solution of the maleic anhydride production residue mixture at a temperature of from about 20° C. to about 250° C. for a holding time may require condensation and reflux of low boiling compounds such as certain alkyl alcohols (e.g., methanol) if these compounds are vaporized when the solution is held at the elevated temperature. The term "holding time" is described elsewhere herein. In some embodiments, contacting the maleic anhydride production residue mixture with an alkyl alcohol solvent in sufficient amount to form a solution and holding the solution for a holding time is conducted at a temperature of from about 20° C. to about 150° C. In some embodiments, the temperature and holding time are controlled to substantially solubilize (e.g., to form a homogeneous solution) the maleic anhydride production residue while limiting the amount of esterification to dialkyl esters. In some embodiments, the temperature and holding time are controlled to substantially solubilize the maleic anhydride production residue and esterify less than 10% (e.g., less than 5%, less than 3%, less than 2%) of the carboxylic acids and anhydrides to dialkyl esters.

Optionally, the alcohol solution of the maleic anhydride production residue mixture can be at least partially esterified, prior to hydrogenation, at an esterification temperature of about 100° C. to about 250° C., with or without esterification catalyst, batch or continuous, by methods known in the art.

The step of hydrogenating the solution in the presence of a hydrogenation catalyst and forming a hydrogenation product can be conducted at a hydrogenation temperature of about 50° C. to about 200° C. under hydrogen pressure of about 50 psig (about 450 kPa) to about 1000 psig (about 7000 kPa) by methods known in the art. In some embodiments, a fixed-bed hydrogenation is conducted. When a fixed-bed hydrogenation is conducted, the pressure drop across the fixed-bed hydrogenation reactor may vary depending on the magnitude of the reactor inlet pressure, requirement for flow distribution across the bed, and so forth. High pressure drop can indicate limited reactor capacity. In general, acceptable values of pressure drop may vary, for example, from about 5% to about 30% of the absolute inlet pressure, for example from about 5% to about 20% of the inlet pressure, for example from about 5% to about 10% of the inlet pressure. A portion of the hydrogenation product, or a portion of the final dialkyl succinate product, may be recycled through the hydrogenation reactor to act as a heat carrier and/or diluent to manage exothermic heat of reaction. It may be desirable to filter the feed (i.e., the alkyl alcohol solution of the maleic anhydride production residue mixture that has been held at a temperature of from about 20° C. to about 250° C. for a holding time) to a fixed-bed hydrogenation reactor to reduce the potential for any solids to damage the feed pump, plug the feed piping, or foul the reactor bed.

Alcohol solvent may optionally be removed from the hydrogenation product to remove water formed as a by-product of esterification reactions. In some process embodiments, the alkyl alcohol solvent is removed from the hydrogenation product in the presence of an esterification catalyst.

The step of treating the hydrogenation product with alcohol and forming a crude product containing dialkyl esters can be conducted at an esterification temperature of about 100° C. to about 140° C., for example about 100° C. to about 110° C., with or without esterification catalyst, batch or continuous, by methods known in the art. In some embodiments, the esterification is completed in the presence of an esterification catalyst. The esterification reaction may be carried out in any suitable reaction apparatus, for example, a continuous stirred tank reactor, a batch reactor, a tubular flow reactor, or a reactive distillation apparatus. It is known that condensation esterification reactions are equilibrium reactions and the extent of esterification may be increased by removing water of reaction. In some embodiments, water of reaction is removed continuously during the esterification reaction. In some embodiments, water is removed in an intermittent fashion such as in a staged process of alternating reaction steps and water removal steps. At higher esterification temperature undesirable by-products may be formed, for example fumarates may form from malic acid. The esterification temperature can be chosen to reduce the formation of dialkyl fumarate, which may be a close boiler to the dialkyl succinate product. Alcohol addition, residence time, and water removal are controlled depending upon the extent of esterification desired, for example to achieve about 85% to 99.9% conversion of carboxylic acids to the corresponding esters, or for example to convert at least 85% of the maleic anhydride, fumaric acid, and their derivatives to dialkyl esters in the crude product, or for example to react the reaction mixture substantially (e.g., more than half way) to equilibrium. Depending on reaction conditions, suitable residence times may be less than about 1 hour to 24 hours, for example about 1 to 12 hours, for example about 1 to 6 hours. In some embodiments, water is removed as vapor using an alcohol (e.g., the alkyl alcohol solvent) as a stripping agent to facilitate removal of water and drive the esterification reaction toward completion.

Isolating dialkyl succinate (e.g., dimethyl succinate, b.p. 196° C.) from the crude product containing dialkyl esters may be difficult by simple distillation. Two impurities that may be present after completing the esterification are dialkyl fumarate (e.g., dimethyl fumarate, b.p. 193° C.) and dialkyl maleate (e.g., dimethyl maleate, b.p. 202° C.). In particular, dialkyl fumarate may be generally present in higher concentration than dialkyl maleate. Additional dialkyl fumarate may form during distillation in the presence of acid at elevated temperature. One possible separation approach would be distillation with many theoretical stages, but such equipment is not always available and requires high investment. Another separation approach is a two-step distillation consisting of a first distillation to quickly separate the desired dialkyl succinate as an overhead product from higher-boiling esterification catalyst (e.g., acid catalyst) and malic esters, followed by a second distillation to purify the dialkyl succinate (i.e., purify the overhead stream from the first distillation). The two-step distillation has the advantage of isolating the dialkyl succinate from any acids before an appreciable amount of elevated-temperature acid-catalyzed reaction can form additional fumarates. In some embodiments, the second distillation is conducted to produce a low-boiling overhead stream enriched in dialkyl fumarate, a side-stream enriched in dialkyl succinate, and a bottoms stream containing higher boiling materials. The side-stream enriched in dialkyl succinate is the purified final product. In some embodiments at least a portion of the low-boiling overhead stream enriched in dialkyl fumarate from the second distillation is recycled to the hydrogenation step to convert dialkyl fumarate to dialkyl succinate. The first distillation and second distillation may be conducted at any pressures (e.g., sub-atmospheric pressures) that provide acceptable separation and purification of the dialkyl succinate. It may be desirable to operate at sub-atmospheric pressure to reduce distillation temperatures and thereby reduce the formation of additional dialkyl fumarate as described above. In some embodiments, the first distillation and the second distillation are operated at pressures of about 50 mmHg absolute or less, for example at pressures from about 10 to 50 mmHg absolute.

In cases where simple distillation is not effective, a combination of distillation with crystallization may be used to remove impurities that have high melting points. For example, in a step of isolating dimethyl succinate, a low-boiling overhead cut enriched in dimethyl fumarate will naturally form crystals of dimethyl fumarate (approximate m.p. 103° C.) upon modest cooling. These crystals may be separated (e.g., by crystallization, by filtration) and the liquid phase or a portion of the liquid phase returned to the distillation column for further purification to isolate product.

Effectively according to the disclosures herein, no pure starting materials are required, such as: pure maleic anhydride, pure maleic monomethyl ester, and pure dimethyl maleate. Similarly, neither is it required to conduct an initial esterification of the mixture from maleic anhydride production byproduct residues, followed by the hydrogenation of the resulting monoester and without esterification to form the dialkyl succinate. And lastly, no purification of the mixture from maleic anhydride production byproduct residues is required prior to the hydrogenation.

Further according to the disclosures herein, an undesirable and generally not utilized co-product from maleic anhydride manufacturing is converted into useful succinate diesters. The mixture from maleic anhydride production residue is converted to more than 80 wt % dialkyl succinate products by hydrogenation and esterification at surprisingly high conversions.

Succinate dialkyl esters are known to have good utility as solvents with a low VOC (volatile organic compounds) rating and serve as synthetic starting materials for pigments and pharmaceuticals. Volatile Organic Compounds (VOCs) is a term, often used in a regulatory context, applied to organic chemicals entering the atmosphere as a consequence of their use in consumer and industrial products and processes. VOCs are known air pollutants which undergo photochemical reactions leading to formation of smog and ground-level ozone. There is a growing realization that some VOCs have a more significant effect on ozone than others. As a result, regulations being promulgated (e.g. California aerosol coatings regulations) take into account differences in photochemical reactivity, effectively restricting use of more reactive VOCs while encouraging use of less-reactive VOCs.

The US EPA (Environmental Protection Agency) is making some VOCs exempt from VOC regulations based upon their lower photochemical reactivity. An increasing competitive advantage in the marketplace exists now for organic solvents with lower photochemical reactivity versus those with higher photochemical reactivity. One measure of photochemical reactivity that has become widely accepted is "Maximum Incremental Reactivity" (MIR), representing the maximum weight of ozone formed when a reactive VOC is added to a baseline mix (MIR is expressed as grams of ozone per gram of reactive VOC). MIR values for a wide variety of VOCs have been measured or calculated and made publically available see: e.g. State of California, USA, Aerosol coating Products Regulation; Subchapter 8.6 Maximum Incremental Reactivity, Art. 1. 94700, MIR Values for Compounds. Dimethyl succinate (DMS) is known to have a low, more desirable, MIR value of only 0.23 grams of ozone per gram of DMS.

In some embodiments, the disclosures herein provide a continuous process for making dialkyl succinate from a mixture comprising substantially a maleic anhydride production residue and isolating at least a portion of dialkyl succinate. For the purpose of carrying out a continuous hydrogen of the maleic anhydride production residue solution, a sample of the production residue solid is dissolved in an alkyl alcohol (e.g. methanol) and the resulting solution provided to a vessel 20 indicated in FIG. 1. The vessel 20 is a thermally insulated pressure tube packed with a hydrogenation catalyst (e.g., palladium on carbon). An 18% by weight solution in methanol is pumped using pumping means 80 from vessel 100 containing this solution and through the vessel 20 at a flow rate of 210 grams per hour along with a 3 times the molar amount of hydrogen (from vessel 40 in FIG. 1) under 80 psig (653 kPa) hydrogen pressure at 80° C. by means of mass flow controller 60 and associated pressure measuring apparatus and over-pressure relief valving (not shown). The vessel 20 is heated by means of a heating mantel 120 (or the equivalent means known in the art) and temperature is measured by means of a temperature measurement device 140 which includes one or more thermocouples (or the equivalent means known in the art). Pressure in the reactor is regulated by means of regulator 180. Cooling of the product stream is provided by coils 200 (or the equivalent means known in the art). A liquid-gas separator 220 removes gases 230 (e.g., unreacted hydrogen) and product is delivered to a vessel 240.

The term "hydrogenation catalyst" refers to any catalyst that is effective in hydrogenating carbon-carbon double bonds in the presence of carboxylic acids, carboxylic esters, and aliphatic alcohols. In some embodiments, the hydrogenation catalyst is a transition metal catalyst. In some embodiments, the hydrogenation catalyst comprises a Group VIII metal (e.g., platinum, palladium, rhodium, ruthenium, nickel, cobalt, iron, and the like). The hydrogenation catalyst may be in various forms such as unsupported powdered metal, activated skeletal catalysts (e.g., Raney® catalysts, sponge, Urushibara catalysts), supported catalysts (e.g., Group VIII metal on carbon). In some embodiments, the hydrogenation catalyst is a supported catalyst. In some embodiments, the hydrogenation catalyst is palladium on a carbon support. In some embodiments, the hydrogenation catalyst is palladium on monolith carbon support. In some embodiments, the hydrogenation catalyst is palladium on a silica support. The hydrogenation catalyst can be used in various hydrogenation applications (e.g., slurry, fixed bed, fluidized bed, and the like).

The term "esterification catalyst" refers to any catalyst that is effective in esterifying carboxylic acids to carboxylic esters. In some embodiments, the esterification catalyst is an acid catalyst. In some embodiments, the catalyst is a strong Lewis acid or Bronsted acid (e.g., sulfuric acid, sulfonic acid). In some embodiments the catalyst is methanesulfonic acid, xylenesulfonic acid, para-toluene sulfonic acid, or benzene sulfonic acid. In some embodiments, the catalyst is a transition metal catalyst (e.g., titanium- or tin-based).

The term "holding time", as used herein, can be determined by measuring the amount of time required to hold the solution of maleic anhydride production residue in alkyl alcohol solvent at the elevated temperature in order to maintain an acceptable pressure drop in a downstream fixed-bed hydrogenation reactor during a run time of at least 1000 hours. Alternatively, "holding time" can be determined by measuring the amount of time needed to open at least 20 percent, for example 30 percent, 50 percent or higher of the maleic anhydride to the corresponding monoalkyl ester. Acceptable values of pressure drop are described elsewhere herein. Examples of holding time include 1 second to 12 hours, for example 1 minute to 12 hours, for example 5 minutes to 2 hours.

As used herein, the term "b.p." refers to atmospheric boiling point.

As used herein, the term "m.p." refers to melting point.

As used herein, the term "OD" refers to outside diameter and the term "ID" refers to inside diameter.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features that may be readily separated from or combined with the features of any of the other several embodiments without departing from the scope or spirit of the present disclosure. Any recited method can be carried out in the order of events recited or in any other order that is logically possible.

Embodiments of the present disclosure employ, unless otherwise indicated, techniques of chemistry, and the like, which are within the skill of the art. Such techniques are explained fully in the literature.

Unless indicated otherwise: parts are parts by weight, concentration in % is % by weight, temperature is in ° C., and pressure is in atmospheres. Pressures reported in pounds per square inch gauge (psig) include the pressure of one atmosphere (14.7 pounds per square inch). One atmosphere is equivalent to 14.7 pounds per square inch absolute or 0 pounds per square inch gauge. Standard temperature and pressure are defined as 25° C. and 1 atmosphere.

It is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

As used herein, for both the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

TEST METHODS

Gas chromatography (GC) and proton NMR (nuclear magnetic resonance) are used to characterize and to analyze reaction products in the manner known to the skilled person. All gas chromatographic (GC) analysis may be performed using an AGILENT TECHNOLOGIES 6890 equipped with AGILENT DB-5, DB-1701, or HP-FFAP columns, helium (He) carrier gas, and flame ionization detectors. All NMR analysis may be performed using a VARIAN, Inc. 500-MR (500 MHz magnet) or 600-MR (600 MHz magnet) spectrometer and software.

EXAMPLES

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for.

The following examples are provided to illustrate the present invention. The examples are not intended to limit the scope of the present invention and should not be so interpreted. It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also the individual concentrations (e.g., 1%, 2%, 3%, and 4%) and the sub-ranges (e.g., 0.5%, 1.1%, 2.2%, 3.3%, and 4.4%) within the indicated range. The term "about" can include ±1%, ±2%, ±3%, ±4%, ±5%, ±8%, or ±10%, of the numerical value(s) being modified. In addition, the phrase "about 'x' to 'y'" includes "about 'x' to about 'y'".

Example 1

Mixtures are subjected to hydrogenation in methanol in the following manner. First taking a mixture substantially comprising a maleic anhydride production residue of about: 30 to 90 wt % maleic anhydride, 5 to 68 wt % fumaric acid, 0.4 to 2 wt % maleic acid, 0.1 to 0.5 wt % succinic anhydride, 0.05 to 0.5 wt % succinic acid, 0.1 to 1 wt % phthalic anhydride, 0.1 to 0.5 wt % fumaric monoaldehyde, 0.1 to 0.5 wt % 5-hydroxy-2-furanone, 0.5 to 1.5 wt % malic acid, 0.1 to 0.3 wt % o-xylene, 0.02 to 0.1 wt % acetic acid, 0.1 tot wt % octadecanoic acid, trace amount of methanol, 250 ppm by weight chloride, less than 100 ppm by weight bromide, and some unknown organic compounds and dissolving eight (8) grams of this solid mixture in 32 grams of methanol and placing it into a stainless steel tube reactor containing 0.01 gram of 5 wt % palladium on carbon catalyst. This reactor is purged several times with hydrogen, sealed, and placed in a shaker-agitator. The reactor is heated up to 80° C. using an electric resistive heating tape on the reactor outer wall under 70 psig (584 kPa) hydrogen pressure, while being agitated at 200 agitation cycles per minute. After 2.5 hours, the heater is turned off, and the pressure is released gradually. After filtering out the catalyst, the reaction solution is analyzed by GC (gas chromatography) in the known method. The known NMR method is also used to characterize the product after stripping off methanol solvent. NMR shows that the hydrogenation conversion is 99.7%. GC shows the main products to be dimethyl succinate (DMS) and monomethyl succinate (MMS) in a 29:71 (wt:wt) ratio.

Example 2

Example 1 is reproduced but with following variations in procedure: Eight (8) grams of the identical solid mixture from Example 1 is dissolved in 32 grams of methanol and is placed into the same stainless steel tube reactor containing 0.01 gram of 5 wt % palladium on carbon catalyst. The reactor is purged several times with hydrogen, sealed, and placed in a shaker. The reactor is heated this time up to 70° C. using a heating tape under 70 psig (584 kPa) hydrogen pressure, agitation is at 200 agitation cycles per minute. After 6.7 hours, the heater is turned off, and the pressure is released gradually. After filtering out the catalyst, the reaction solution is analyzed by GC. The NMR method is also used to characterize the product after stripping off methanol. NMR shows that the hydrogenation conversion is 98.8%. GC shows the main products to be dimethyl succinate and monomethyl succinate in a 29:71 (wt:wt) ratio.

Example 3

Eight (8) grams of the identical solid mixture from Example 1 is dissolved in 32 grams of isopropanol and is placed into the same stainless steel tube reactor containing 0.01 gram of 5 wt % palladium on carbon catalyst. The reactor is purged several times with hydrogen, sealed, and placed in a shaker. The reactor is heated this time up to 80° C. using a heating tape under 80 psig (653 kPa) hydrogen pressure, agitation is at 200 agitation cycles per minute. After 18 hours, the heater is turned off, and the pressure is released gradually. After filtering out the catalyst, the reaction solution is analyzed by GC. The NMR method is also used to characterize the product after stripping off methanol. The hydrogenation conversion is 97% and 97 wt % succinic monoisopropyl ester is present in the product mixture.

Example 4

For the purpose of carrying out a continuous hydrogenation of the solution prepared as in the prior examples, e.g. taking a weighed sample of the identical solid mixture from Example 1 and dissolving in a specific mass of methanol and placing the solution into a vessel 20 indicated in FIG. 1, the hydrogenation is conducted in the following way. The vessel 20 is a vertical, thermally insulated pressure tube of 316 stainless steel with 1.73 cm internal diameter and 50.8 cm length packed with 10 grams of 1% by weight palladium on carbon catalyst. An 18% by weight solution in methanol is filtered (not shown) and pumped using pumping means 80 from vessel 100 containing this solution and through the vessel 20 at a flow rate of 150 milliliters per hour along with a 3 times the molar amount of hydrogen (from vessel 40 in FIG. 1) under 80 psig (653 kPa) hydrogen pressure at 80° C. by means of mass flow controller 60 and associated pressure measuring apparatus and over-pressure relief valving (not shown). The vessel 20 is heated by means of a heating mantel 120 (or the equivalent means known in the art) and temperature is measured by means of a temperature measurement device 140 which includes one or more thermocouples (or the equivalent means known in the art). Pressure in the reactor is regulated by means of regulator 180. Cooling of the product stream is provided by coils 200 (or the equivalent means known in the art). A liquid-gas separator 220 removes gases 230 (e.g., unreacted hydrogen) and product is delivered to a vessel 240. A GC analysis of the product shows a conversion of 99.5% based upon mass of solid used in preparation of the solution.

Example 5

The esterification of the hydrogenation product obtained as in Example 1 is carried out in the following manner. A composite sample of the hydrogenation product, obtained from several runs described in Example 1, weighing 144.9 grams is combined with 0.486 gram para-toluene sulfonic acid and added to a 250 milliliter 3-neck round bottom flask. The flask is equipped with apparatus for distillation, means for feeding methanol and a thermocouple for sensing temperature. The methanol solvent is distilled off upon heating the flask to about 70° C. Following distillation, the flask is heated to 110° C., and methanol is further provided to continue the esterification. After 1 hour at 110° C., 99.5% of the acid is converted to dimethyl ester. GC and NMR are used to characterize the crude dimethyl succinate present in the product.

Example 6

500 gram of the identical solid mixture from Example 1, 300 gram anhydrous methanol, and 5.6 gram xylene sulfonic acid catalyst (90% by weight purity) are charged into a 2 liter four neck flask equipped with apparatus for distillation, means for feeding methanol and thermocouples for sensing mixture temperature and overhead temperature of methanol distillate. The mixture is heated up to 110° C. and then additional methanol is pumped in at a rate of 3.5 grams/minute while removing wet methanol overhead. After 5 hours, the esterification reaction is completed with an acid number of 8.1 milligram KOH/gram sample.

Example 7

The ester mixture produced in Example 6 is dissolved in dimethyl succinate at 8 wt %, filtered through a 2 micron filtering paper, and pumped at a rate of 3.5 gram/minute into a fixed bed reactor containing 14 grams palladium catalyst at 80° C. under 150 psig (1136 kPa) hydrogen pressure. A GC analysis of the product shows a 97 to 98% conversion of unsaturated $C_4$ diacid derivatives to saturated $C_4$ diacid derivatives.

Example 8

172 grams of the hydrogenation product from Example 3 and 0.39 gram xylene sulfonic acid catalyst (90% by weight purity) are charged into a 500 mL four neck flask equipped with apparatus for distillation, means for feeding isopropanol and thermocouples for sensing mixture temperature and overhead temperature of isopropanol distillate. The mixture is heated up to 110° C. while wet isopropanol is distilled overhead. Then additional isopropanol is pumped in at a rate of 3.5 grams/minute and wet isopropanol is continuously removed overhead. After 10 hours, the esterification reaction is completed with an acid number of 9.86 milligram KOH/gram sample. The product is purified by vacuum distillation to obtain 98 wt % diisopropyl succinate.

Example 9

10 wt % maleic anhydride production residue of Example 1 is dissolved in isopropanol by heating the mixture up to reflux and maintained at reflux for 15 minutes. The solution is cooled to room temperature and filtered through a 2 micron filtering paper. The filtered solution is pumped at a rate of 3.5 grams/minute into a 0.75 inch OD×0.68 inch ID (1.90 cm OD×1.73 cm ID) fixed bed reactor made of 316 stainless steel and packed with 14 grams of 1 wt % palladium on silica extrudates (approximately 0.5 grams/mL apparent density) at 130° C. under 700 psig (4930 kPa) hydrogen pressure. Exit temperature is 146° C. The hydrogenation conversion is >99%.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A process for making dialkyl succinate, comprising:
   a. providing a mixture comprising about 30 to 90 wt % maleic anhydride and about 5 to 68 wt % fumaric acid;
   b. contacting the mixture of (a) with an alkyl alcohol solvent in sufficient amount to form a solution and holding the solution at a temperature of from about 20° C. to about 250° C. for a holding time;
   c. hydrogenating the solution of (b), in the absence of an intermediate distillation between (b) and (c), at hydrogenation conditions of temperature from about 50 to 200° C. under hydrogen pressure from about 50 to 1000 psig (about 450 to 7000 kPa) in the presence of a hydrogenation catalyst to form a hydrogenation product;
   d. treating the hydrogenation product with alcohol at an esterification temperature of about 100° C. to 140° C. to form crude product containing dialkyl esters, wherein at least 85 percent of maleic anhydride, fumaric acid and their derivatives of (a) have been converted to dialkyl esters in the crude product; and
   e. isolating dialkyl succinate from the crude product of (d).

2. The process of claim 1 wherein the mixture of (a) further comprises about 0.4 to 2 wt % maleic acid.

3. The process of claim 2 wherein the mixture of (a) further comprises about 0.1 to 0.5 wt % succinic anhydride.

4. The process of claim 3 wherein the mixture of (a) further comprises about 0.05 to 0.5 wt % succinic acid.

5. The process of claim 4 wherein the mixture of (a) further comprises about 0. 1 to 1 wt % phthalic anhydride.

6. The process of claim 5 wherein the mixture of (a) further comprises about 0.1 to 0.5 wt % fumaric monoaldehyde.

7. The process of claim 6 wherein the mixture of (a) further comprises about 0.1 to 0.5 wt % 5-hydroxy-2-furanone.

8. The process of claim 7 wherein the mixture of (a) further comprises about 0.5 to 1.5 wt % malic acid.

9. The process of claim 8 wherein the mixture of (a) further comprises about 0.1 to 0.3% o-xylene.

10. The process of claim 9 wherein the mixture of (a) further comprises about 0.02 to 0.1 wt % acetic acid.

11. The process of claim 1 wherein the mixture comprising about 30 to 90 wt % maleic anhydride and about 5 to 68 wt % fumaric acid is maleic anhydride production residue.

12. The process of claim 1 wherein the hydrogenation catalyst comprises palladium.

13. The process of claim 1 wherein at least one of the contacting (b) or the esterification (d) is carried out in the presence of an esterification catalyst.

14. The process of claim 13 wherein the esterification catalyst is an acid catalyst.

15. The process of claim 1, wherein isolating dialkyl succinate from the crude product containing dialkyl esters is conducted by distillation.

16. The process of claim 15, wherein the distillation comprises:
   a. distilling in a first distillation column the crude product containing dialkyl esters to separate a low-boiling overhead stream enriched in dialkyl esters from high-boiling acids and esters;
   b. distilling in a second distillation column the low-boiling overhead stream enriched dialkyl esters from the first distillation column to produce a low-boiling overhead stream enriched in dialkyl fumarate, a side-stream enriched in dialkyl succinate, and a bottoms stream containing higher boiling materials; and
   c. withdrawing the side-stream enriched in dialkyl succinate as the product.

17. The process of claim 16 wherein at least a portion of the low-boiling overhead stream enriched in dialkyl fumarate is recycled to the hydrogenating step.

18. The process of claim 15, wherein the distillation comprises:
   a. distilling in a distillation column the crude product containing dialkyl esters to produce a low-boiling overhead stream enriched in dialkyl fumarate;
   b. cooling the low-boiling overhead stream enriched in dialkyl fumarate to form condensed liquid and solids;
   c. separating the solids from the condensed liquid to form a condensed liquid substantially free of solids;
   d. returning at least a portion of the condensed liquid substantially free of solids to the distillation column.

19. The process of claim 18, wherein separating the solids from the condensed liquid to form a condensed liquid substantially free of solids is conducted by filtration.

20. The process of claim 18, wherein separating the solids from the condensed liquid to form a condensed liquid substantially free of solids is conducted by crystallization.

21. The process of claim 1 wherein at least 95 weight percent of maleic anhydride, fumaric acid and their derivatives of (a) have been converted to dialkyl esters in the crude product.

* * * * *